US006432967B1

(12) United States Patent
Sandborn

(10) Patent No.: US 6,432,967 B1
(45) Date of Patent: *Aug. 13, 2002

(54) ENEMA AND ENTERICALLY-COATED ORAL DOSAGE FORMS OF AZATHIOPRINE

(75) Inventor: William J. Sandborn, Rochester, MN (US)

(73) Assignee: Mayo Foundation for Medical Education & Research, Rochester, MN (US)

( * ) Notice: Subject to any disclaimer, the term of this patent is extended or adjusted under 35 U.S.C. 154(b) by 5 days.

This patent is subject to a terminal disclaimer.

(21) Appl. No.: 09/819,051

(22) Filed: Dec. 21, 2000

Related U.S. Application Data

(60) Continuation of application No. 09/310,505, filed on May 2, 1999, now Pat. No. 6,166,024, which is a continuation-in-part of application No. 08/905,490, filed on Aug. 1, 1997, now Pat. No. 5,905,081, which is a division of application No. 08/413,505, filed on Mar. 30, 1995, now Pat. No. 5,691,343.

(51) Int. Cl.[7] .............................................. A61K 31/52
(52) U.S. Cl. ....................................................... 514/262
(58) Field of Search ......................................... 514/262

(56) References Cited

U.S. PATENT DOCUMENTS

| | | | |
|---|---|---|---|
| 3,056,785 A | 10/1962 | Hitchings et al. ........... 260/252 |
| 3,983,233 A | 9/1976 | Brattsand et al. ........... 424/241 |
| 3,996,359 A | 12/1976 | Brattsand et al. ........... 424/241 |
| 4,289,750 A | 9/1981 | Kopp et al. | |
| 4,350,690 A | 9/1982 | Kumana ....................... 424/243 |
| 4,451,454 A | 5/1984 | Wong | |
| 4,496,553 A | 1/1985 | Halskov | |
| 4,627,851 A | 12/1986 | Wong et al. ................. 604/892 |
| 4,632,911 A | 12/1986 | Bauer | |
| 4,642,111 A | 2/1987 | Sakamoto et al. | |
| 4,687,667 A | 8/1987 | Rhodes et al. ........... 424/195.1 |
| 4,744,987 A | 5/1988 | Mehra et al. | |
| 4,880,830 A | 11/1989 | Rhodes ....................... 424/470 |
| 4,980,173 A | 12/1990 | Halskov | |
| 5,026,559 A | 6/1991 | Eichel et al. | |
| 5,108,758 A | 4/1992 | Allwood et al. ............ 424/468 |
| 5,401,512 A | 3/1995 | Rhodes et al. .............. 424/458 |
| 5,468,503 A | 11/1995 | Yamada et al. | |
| 5,498,608 A | 3/1996 | Johnson et al. ............. 514/150 |
| 5,514,663 A | 5/1996 | Mandel | |
| 5,536,507 A | 7/1996 | Abramowitz et al. ....... 424/479 |
| 5,541,170 A | 7/1996 | Rhodes et al. .............. 514/166 |
| 5,541,171 A | 7/1996 | Rhodes et al. .............. 514/166 |
| 5,556,964 A | 9/1996 | Hofstraat et al. | |
| 5,582,837 A | 12/1996 | Shell .......................... 424/451 |
| 5,631,022 A | 5/1997 | Mandel et al. | |
| 5,633,274 A | 5/1997 | Halperin et al. ............ 514/405 |
| 5,643,602 A | 7/1997 | Ulmius ....................... 424/462 |
| 5,651,983 A | 7/1997 | Kelm et al. | |
| 5,656,290 A | 8/1997 | Kelm et al. | |
| 5,670,158 A | 9/1997 | Davis et al. | |
| 5,686,105 A | 11/1997 | Kelm et al. | |
| 5,686,106 A | 11/1997 | Kelm et al. | |
| 5,691,343 A | 11/1997 | Sandborn | |
| 5,716,648 A | 2/1998 | Halskov et al. ............. 424/682 |
| 5,792,795 A | 8/1998 | Buser et al. ................ 514/560 |
| 5,814,336 A | 9/1998 | Kelm et al. | |
| 5,843,479 A | 12/1998 | Kelm et al. | |
| 5,843,929 A | 12/1998 | Larson et al. ............... 514/182 |
| 5,856,095 A | 1/1999 | Evans et al. | |
| 5,889,028 A | 3/1999 | Sandborn et al. ........... 514/343 |
| 5,908,833 A | 6/1999 | Brattsand et al. | |

FOREIGN PATENT DOCUMENTS

EP          0 054 010 B1     8/1985

(List continued on next page.)

OTHER PUBLICATIONS

Mayer et al, "Status of Adjuvant Therapy for Colorectal Cancer", Derwent Drug File Abstracts, abstract No. 1989–44780, 1989.*

Sartorelli, et al. "Biochemical approaches to the combination chemotherapy of colon cancer" Dec. 1975, *Cancer*.

Kitamura, et al. "Effective Chemotherapy for Abdonmical Desmoid Tumor in a Patient with Gardner's Syndrome" Sep. 1991, *Dis Colon Rectum*.

Danielsson, A., et al., "A controlled randomized trial of budesonide versus prednisolone retention enemas in active distal ulcerative colitis." Scandinavian Journal of Gastroenterology Supplement, vol. 22, No. 8, pp. 987–992 (1987).

Higuchi, T., et al., "Phase–solubility techniques." Advances in Analytical Chemistry and Instrumentation, vol. 4, pp. 117–212 (1964).

Johansson, S.A., et al., "Topical and systemic glucocorticoid potencies of budesonide, beclomethasone dipropionate and prednisolone in man." European Journal of Respiratory Diseases, vol. 63, Suppl. 122, pp. 74–82 (1982).

Kato, Y., et al., "Enhanced bioavailability of 6–mercaptopurine after rectal administration in rats." Pharmaceutical Research, vol. 9, No. 5, pp. 697–699 (1992).

Krasznai, A., et al., "Decreased number of steroid receptors of circulating lymphocytes in Crohn's Disease and ulterative colitis." Haematologia, vol. 19, No. 4, pp. 299–301 (1986).

Pearson, D.C., et al., "Azathioprine and 6–mercaptopurine in Crohn's disease—a meta–analysis." Ann. Intern. Med., vol. 123, No. 2, pp. 132–142 (1995).

Yokoyama, T., et al., "Studies on drug nonequivalence. X. bioavailability of 6–mercaptopurine polymorphs." Chem. Pharm. Bull., vol. 29, No. 1, pp. 194–199 (1981).

Zins, B.J., et al., "A dose–ranging study of azathioprine pharmacokinetics after single–dose administration of a delayed–release oral formulation." J. Clin. Pharmacol., No. 37, pp. 38–46 (1997).

(List continued on next page.)

*Primary Examiner*—William R. A. Jarvis
(74) *Attorney, Agent, or Firm*—Fish & Richardson P.C.

(57) ABSTRACT

This invention relates to enema and enterically-coated dosage forms having an amount of azathioprine effective to prevent colorectal adenomas without dose-limiting systemic toxicity.

3 Claims, No Drawings

FOREIGN PATENT DOCUMENTS

| EP | 0 343 993 A1 | 11/1989 |
|---|---|---|
| EP | 0 143 764 B1 | 6/1990 |
| EP | 0 381 414 A3 | 8/1990 |
| EP | 0 381 414 A2 | 8/1990 |
| EP | 0 232 690 B1 | 10/1990 |
| EP | 0 278 174 B1 | 3/1993 |
| EP | 0395329 B2 | 1/1999 |
| JP | 6-24962 | 2/1994 |
| WO | WO 83/00435 | 2/1983 |
| WO | WO 91/04018 | 4/1991 |
| WO | WO 91/07949 | 6/1991 |
| WO | WO 92/09270 | 6/1992 |
| WO | WO 92/14452 | 9/1992 |
| WO | WO 94/06414 | 3/1994 |
| WO | WO 94/18973 | 9/1994 |
| WO | WO 94/27582 | 12/1994 |
| WO | WO94/28911 | 12/1994 |
| WO | WO 96/04014 | 2/1996 |
| WO | WO 96/30021 | 10/1996 |
| WO | WO 96/36314 A2 | 11/1996 |
| WO | WO 96 36314 A2 | 11/1996 |
| WO | WO 96/36319 | 11/1996 |
| WO | WO 96/36321 | 11/1996 |
| WO | WO 96/36322 | 11/1996 |
| WO | WO 97/03667 | 2/1997 |
| WO | WO 97/34608 | 9/1997 |
| WO | WO 99/16454 | 4/1999 |

OTHER PUBLICATIONS

Zins, B.J., et al., "Azathioprine pharmacokinetics following single dose IV, oral, delayed–release oral, and rectal foam administration." Abstract of Meetings of the AGA, AASLD at Digestive Disease Week, San Diego, CA, (May 14–17, 1995.

Abstract of Japanese Patent Publication No. 62 072618, issued Apr. 3, 1987, (Takada), from Database WPI, Derwent Publications Ltd., London, England.

Adamson, P.C., et al., "A phase II trial of continous–infusion 6–mercaptopurine for childhood solid tumors", *Cancer Chemother Pharmacol*, 26, 343–344 (1990).

Arndt, C.S., et al., "Bioavailability of low–dose 6–mercaptopurine", *Clin. Pharmacol. Ther.*, 43, 588–591 (May 1988).

Candy, S., et al., "A double–blind controlled study of azathioprine in the treatment and maintenance of remission in Crohn's disease", *Gastroenterology*, 106, A659 (Apr. 1994).

Caprilli, R., et al., "A double–blind comparison of the effectiveness of azathioprine and sulfasalazine in idiopathic proctocolitis. Preliminary Report", *Dig. Dis.*, 20, 115–120 (1975).

Chan, G.C., et al., "Azathioprine Metabolism: Pharmacokinetics of 6–Mercaptopurine, 6–Thiouric Acid and 6–Thioguanine Nucleotides in Renal Transplant Patients",*J. Clin. Pharmacol*, 30, 358–363, (1990).

Connell, W.R., et al., "Bone Marrow Toxicity caused by azathioprine in inflammatory bowel disease: 27 years of experience", *Gut*, 34, 1081–1085 (1993).

Ewe, K., et al., "Azathioprine combined with prednisolone or monotherapy with prednisone in active Crohn's disease", *Gastroenterology*, 105, 367–372 (Aug. 1993).

Hawthorne, A.B., et al., "Randomised controlled trial of azathioprine withdrawl in ulcerated colitis", *Brit. J. Med.*, 305, 20–22 (1992).

Jewell, D.P., et al., "Azathioprine in ulcerative colitis: final report on controlled therapeutic trial", *Br. Med. J.*, 4, 627–639 (1974).

Kirk, A.P., et al., "Controlled trial of azathioprine in chronic ulcerative colitis", *Br. Med. J.*, 284, 1291–1292 (1982).

Klein, M., et al., "Treatment of Crohn's Disease with Azathioprine: A Controlled Evaluation", *Gastroenterology*, 66, 916–922 (1974).

Korelitz, B.I., et al., "Favorable Effect of 6–Mercaptopurine on Fistulae of Crohn's Disease", *Digestive Diseases and Sciences*, 30, 58–64 (Jan. 1985).

Korelitz, B.I., et al., "Shortcomings of the National Crohn's Disease Study: The Exclusion of Azathioprine Without Adequate Trial", *Gastroenterology*, 80, 193–194 (1981).

Lennard, L., et al., "Azathioprine metabolism in kidney transplant recipients", *Br. J. Clin. Pharmac*, 18, 693–700 (1984).

Markowitz, J., et al., "Long–Term 6–Mercaptopurine Treatment in Adolescents with Crohn's Disease", *Gastroenterology*, 99, 1347–1351 (1990).

Nyman, M., et al., "Long–Term Immunosuppresive Treatment in Crohn's Disease", *Canadian J. Gastroenterology*, 20, 1197–1203 (Nov. 10, 1985).

O'Donoghue, D.P., et al., "Double–Blind Withdrawl Trial of Azathioprine as Maintenance Treatment for Crohn's Disease", *The Lancet*, 955–957 (Nov. 4, 1978).

Odlind, B., et al., "Serum Azathioprine and 6–Mercaptopurine Levels and Immunosuppresive Activity after Azathiprine in Uremic Patients", *Int. J. Immunoopharmac*, 8, 1–11 (1986).

Perrault, J., et al., "6–Mercaptopurine Therapy in Selected Cases of Corticosteriod–Dependent Crohn's Disease", *May Clin. Proc.*, 66, 480–484 (1991).

Present, D.H., et al., "6–Mercaptopurine in the Management of inflammatory Bowel Disease: Short and Long Term Toxicity", *Annals of Internal Medicine*, 111, 641–649 (Oct. 15, 1989).

Present, D.H., et al., "Treatment of Crohn's Disease with 6–Mercaptopurine", *N. Engl. J. Med.*, 302, 981–987 (May 1, 1980).

Rhodes, J., et al., "Controlled Trial of Azathioprine in Crohn's Disease", *The Lancet*, 1273–1276 (Dec. 11, 1971).

Rosenberg, J.L., et al., "A controlled trial of azathioprine in the management of chronic ulcerative colitis", *Gastroenterology*, 69, 96–99 (1975).

Rosenberg, J.L., et al., "A Controlled Trial of Azathiprine in Crohn's Disease", *Digestive Diseases*, 20, 721–726 (Aug. 1975).

Singleton, J.W., "Azathioprine Has a Very Limited Role in the Treatment of Crohn's Disease", *Digestive Diseases and Sciences*, 26, 368–371 (Apr. 1981).

Summers, R.W., et al., "National Cooperative Crohn's Disease Study: Results of Drug Treatment", *Gastroenterology*, 77, 847–869 (1979).

Sutherland, L.R., "Topical treatment of ulcerative colitis", *Med. Clin. North Am.*, 74, 119–131 (Jan. 1990).

Takeichi, Y., et al., "Improvement of aqueous solubility and rectal absorption of 6–mercaptopurine by addition of sodium benzoate", *Biol. Pharm. Bull.*, 17, 1391–1394 (Oct. 1994).

Verhave, M., et al., "Azathioprine in the treatment of children with inflammatory bowel disease", *J. Pediatrics*, 117, 809–814 (Nov. 1990).

Willoughby, J.T., et al., "Controlled Trial of Azathioprine in Crohn's Disease", *The Lancet*, 944–946, (Oct. 30, 1971).

Wilson, E.P., et al., "Azathioprine", *Analytical Profiles of Drug Substances,* vol. 10; K. Florey, Ed; Academic Press: New York, 30–53, (1981).

Zimm, S., et al., "Phase I and Clinical Pharmacological Study of Mercaptopurine Administered as a Prolonged Intravenous Infusion", *Cancer Research,* 45, 1869–1873 (Apr. 1985).

Zimm, S., et al., "Variable Bioavailability of Oral Mercaptopurine", *N. Eng. J. Med.,* 308, 1005–1009 (1983).

Anderson et al., "In Vitro Biotransformation of Glucocorticoids in Liver and Skin Homogenate Fraction from Man, Rat and Hairless Mouse, " *J. Steroid Biochem.,* vol. 16, pp. 787–795 (1982).

S. Bondesen et al., "Absorption of 5–aminosalicyclic from colon and rectum," *Br. J. Clin. Pharmac.,* (1988), 25, 269–272.

Bostrom et al., "Cellular Pharmacology of 6–Mercaptopurine in Acute Lumphoblastic Leukemia," *The American Journal of Pediatric Hematology/Oncology,* 15(1): 80–86 (1993).

A. H. Chalmers, "Studies on the Mechanism of Formation of 5–Mercapto–1–Methyl–4–Nitroimidazole, A Metabolite of the Immunosuppresssive Drug Azathioprine," *Biochemical Pharmacology,* vol. 23, pp. 1891–1901, 1974.

Laurie D. DeLeve et al., "Glutathione Metabolism and Its Role in Hepatotoxicity," *Pharmac. Ther.,* vol. 52, pp. 287–305 (1991).

B. Norlander et al., "Pharmacokinetics of a 5–aminosalicyclic acid enteric–coated tablet in patients with Crohn's disease or ulcerative colitis and in healthy volunteers", *Ailment. Pharmacol. Therap.,* (1990) 4, 497–505.

Y. Kato et al., "Rectal bioavailability of 6–mercaptopurine in children with acute lymphobastic leukaemia: partial avoidance of "first–pass" metabolism", *Eur. J. Clin. Pharmacol.,* (1992) 42:619–622.

Lynne Lennard et al., "Pharmacogenetics of acute azathioprine toxicity: Relationship to thiopurine methyltransferase genetic polymorphism," *Clinical Pharmacology & Therapeutics,* vol. 46, No. 2, (1989), pp. 149–154.

L. Lennard, "The clinical pharmacology of 6–mercaptopurine," *Eur. J. Clin. Pharmacol.,* (1992) 43:329–339.

J. Liliemark et al., "Determination of Plasma Azathioprine and 6–Mercaptopurine in Patients with Rehumatoid Arthritis Treated with Oral Azathioprine," *Therapeutic Drug Monitoring,* 12:339–343 (1990).

Kenneth W. Schroeder et al., "Coated Oral 5–Aminosalicyclic Acid Therapy for Mildly to Moderately Active Ulcerative Colitis," *The New England Journal of Medicine,* vol. 317, No. 26, pp. 1625–1629, 1987.

J. Herman et al., "Modified Starches as Hydrophilic Matrixes for Controlled Oral Delivery. I. Production and Characterization of Thermally Modified Starches," *Int. Journal of Pharmaceutics,* 56 (1989) 51–63.

Marvin M. Schreiber et al., "Bioactivity of Controlled Release Formulations of Starch–Encapsulated EPTC," *Journal of Controlled Release,* 7 (1988) 237–242.

TJH Clark et al., "Safety of Inhaled Corticosteroids," International Symposium on Corticosteroid Treatment in Allergic Airway Diseases, Oct. 1–2, 1981, European Journal of Respiratory Diseases, Supp. No. 122, vol. 63 (1982).

R.M. Weinshilboum, "Methylation pharmacogenetics: thiopurine methyltransferase as a model system," *Xenobiotica,* 1992, vol. 22, Nos. 9/10, 1055–1071.

W.J. Sandborn, "Azathiprine: State of the Art in Inflammatory Bowel Disease", *Scandinavian Journal of Gastroenterology,* vol. 33, Supp. 225, 1998, pp. 92–99.

SL Wolman, "Use of Oral Budesonide in a Patient with Small Bowel Crohn's Disease and Previous Psudotumor Cerebri Secondary to Steroids," *Scandinavian Journal of Gastroenterology,* vol. 24, Supp. 158, 1989, pp. 146–147.

\* cited by examiner

ENEMA AND ENTERICALLY-COATED ORAL DOSAGE FORMS OF AZATHIOPRINE

CROSS REFERENCE TO RELATED APPLICATIONS

This patent application is a continuation of U.S. patent application Ser. No. 09/310,505, filed May 12, 1999, now U.S. Pat. No. 6,166,024, which is a continuation-in-part of U.S. patent application Ser. No. 08/905,490, filed Aug. 1, 1997 (now U.S. Pat. No. 5,905,081, issued May 18, 1999), which is a divisional of U.S. patent application Ser. No. 08/413,505, filed Mar. 30, 1995 (now U.S. Pat. No. 5,691,343, issued Nov. 25, 1997).

BACKGROUND OF THE INVENTION

Inflammatory bowel disorders or diseases (IBD) encompass a spectrum of overlapping clinical diseases that appear to lack a common etiology. IBD, however, are characterized by chronic inflammation at various sites in the gastrointestinal (GI) tract. Illustrative IBD are regional enteritis (or Crohn's disease), idiopathic ulcerative colitis, idiopathic proctocolitis, and infectious colitis. Most hypotheses regarding the pathogenesis of IBD concern the implication of immunologic, infectious, and dietary factors.

Colorectal cancer is the most common visceral cancer in the United States. The colorectal cancer progresses through clinically recognizable stages from normal mucosa through enlarging and increasingly dyplastic polyps to carcinoma. The precursor relationship of colorectal adenomatous polyps to carcinoma and the high prevalence of adenomas make them an attractive target in chemoprevention trials. Furthermore, endoscopic or surgical removal of polyps does not change the pathogenetic milieu responsible for their growth and development. The recurrence rate for colorectal adenomas ranges from 20–60% by two years. Patients who have undergone surgical resection of a primary colorectal cancer have also been shown to be at high risk of developing metachronous adenomas. Chemoprevention by pharmacologic intervention remains to be established in clinical practice, and there is a continuing need to develop new chemopreventive treatments for colorectal adenomas. 6-mercaptopurine (6MP) and its prodrug azathioprine (AZA) have been used in the treatment of inflammatory bowel disease (IBD) for over 25 years. Multiple controlled trials and a recent meta-analysis support the efficacy of 6MP and AZA in Crohn's disease. See, J. M. T. Willoughby et al., Lancet, ii 944 (1971); J. L. Rosenberg et al., Dig. Dis., 20, 721 (1975). Several controlled trials support the use of AZA in ulcerative colitis, the most recent by Hawthorne and colleagues, in Brit. Med. J., 305, 20 (1992). Both azathioprine and 6-mercaptopurine have also demonstrated anti-tumor activity against a wide variety of transplantable rodent tumors and against hematologic malignancies in man. However, use of 6MP and AZA has been limited by concerns about their toxicities. Dose-related leukopenia is seen in 2–5% of patients treated long-term with 6MP or AZA for IBD. See, for example, D. H. Present et al., Am. Int. Med., 111, 641 (1989); W. R. Connell et al., Gut, 34, 1081 (1993).

Therefore, a need exits for effective, nontoxic therapies for IBD. Furthermore, there is also a need for new chemopreventative treatments for colorectal adenomas.

SUMMARY OF THE INVENTION

The present invention provides new therapeutic methods of treating inflammatory bowel disease (IBD) and colorectal adenomas comprising topically administering to the colon of a patient in need of such treatment, an amount of azathioprine (AZA) effective to relieve the symptoms of said IBD or to prevent colorectal adenomas, either prior to or following endoscopic or surgical removal. Preferably the azathioprine is administered orally, by means of an enteric-coated unit dosage form that selectively releases AZA in the terminal ileum and/or colon of the patient. The AZA can also be effectively administered to the colon by rectal administration of an enema formulation comprising AZA. Due to poor absorption of AZA in the bloodstream from the colon, relatively high doses of AZA can be administered to the afflicted tissue, i.e., in the case of Crohn's disease, ulcerative colitis, or colorectal adenomas without inducing systemic toxicities such as leukopenia, Therefore, effective AZA doses of from about 150–1000 mg can be delivered 1–4 times daily to adult patients (150 mg 1×day–1000 mg 4×day) without undue toxicities (about 2–20 mg/kg AZA doses are administered).

As used herein the term "azathioprine" includes the pharmaceutically acceptable salts thereof, as well as functionally equivalent analysis, derivatives, and metabolites, such as 6-MP and thioguanine. For example, see U.S. Pat. No. 3,056,785, and W. P. Wilson et al., Anal. Profiles of Drug Substances, 10, 29–53 (1981).

DETAILED DESCRIPTION OF THE INVENTION

Colonic administration of drugs has been used to reduce the toxicity associated with oral or IV corticosteroids and oral 5-aminosalicyclate in patients with IBD. This decreased toxicity is believed to be due to reduced systemic bioavailability. Several types of colonic drug delivery systems are currently available, including enemas (L. R. Sutherland et al., Med. Clin. North Amer., 74, 119 (1990)); rectal foams (Drug. Ther. Bull., 29, 66 (1991)); and delayed release oral formulations in the form of Eudragit-coated capsules which dissolve at pH 7 in the terminal ileum (K. W. Schroeder et al., New Engl. J. Med., 317, 1625 (1987)).

The effective amount of azathioprine (AZA) can be topically administered to the colon of the patient by oral ingestion of a unit dosage form comprising an effective amount of AZA which is enterically coated so as to be released from the unit dosage form in the lower intestinal tract, e.g., in the terminal portion of the ileum and in the colon of the patient. Microparticles of AZA may be individually coated and delivered as a suspension in a liquid vehicle, may be encapsulated as a powder or may be compressed into a pill or tablet and swallowed. Alternatively, the azathioprine may be combined with adjuvants employed in solid unit dosage forms, such as fillers and binders, compressed into shaped, solid dosage forms such as pills or tablets, and the pills or tablets treated so as to apply an enteric coating of suitable thickness thereto.

Enteric coatings are those which remain intact in the stomach, but will dissolve and release the contents of the dosage form once it reaches the small intestine. The purpose of an enteric coating is to delay the release of the AZA until it reached the target site of action in the colon. Since the AZA topically-administered to the colonic tissue in this fashion is only about 10% absorbed into the bloodstream, the systemic side-effects of AZA can be avoided or minimized.

Thus, a useful enteric coating is one that remains undissociated in the low pH environment of the stomach, but readily ionizes when the pH rises to about 4 or 5. The most effective enteric polymers are polyacids having a pHa of 3 to 5.

The most extensively use polymer is cellulose acetate phthalate (CAP) which is capable of functioning effectively as an enteric coating. However, a pH greater than 6 usually is required for solubility and thus a delay in drug release may ensue. Another useful polymer is polyvinyl acetate phthalate (PVAP) which is less permeable to moisture and gastric fluid, more stable to hydrolysis and able to ionize at a lower pH, resulting in earlier release of actives in the duodenum.

A more recently available polymer is hydroxypropyl methylcellulose phthalate. This has similar stability to PVAP and dissociates in the same pH range. A further example of currently used polymers are those based on methacrylic acid, e.g., methacrylic acid ester copolymers with acidic ionizable groups, such as Eudragit S-100 (methacrylic acid copolymer). Various systems are available that allow each of these enteric polymers to be applied as aqueous dispersions, thus facilitating the use of aqueous film-coating technology for the enteric coating of pharmaceutical dosage forms.

Another preferred dosage form in the topical administration of AZA to the colon is an enema formulation, which is rectally administered to the lower colon. Useful formulations comprise an effective amount of AZA dissolved or dispersed in a suitable flowable carrier vehicle, such as water, alcohol or an aqueous-alcoholic fluid. The carrier vehicle is preferably thickened with natural or synthetic thickness such as gums, acrylates or modified celluloses. The formulation can also comprise an effective amount of a lubricant such as a natural or synthetic fat or oil, i.e., a tris-fatty acid glycerate or lecithin. Nontoxic nonionic surfactants can also be included as wetting agents and dispersants. Unit dosages of enema formulations can be administered from prefilled bags or syringes. The carrier vehicle may also comprise an effective amount of a foaming agent such as n-butane, propane or i-butane. Such formulations can be delivered from a pressurized container, so that the vehicle is delivered to the colon as a foam, which inhibits its release from the target site.

Generally, once colorectal polyps are identified, they are endoscopically or surgically removed. Chemoprevention follows removal. However, patients at high risk to develop colorectal polyps could benefit from chemoprevention prior to identification of the adenomas. Such patients may have a strong family history of colorectal polyps or cancer, presence of long-standing extensive ulcerative colitis, or family cancer syndromes such as familial adenomatous polyposis or Lynch Syndrome. In these situations, delayed release oral AZA would result in a decreased frequency of the development of colorectal polyps.

The invention will be further described by reference to the following detailed examples.

EXAMPLE 1

Preparation of Hydrophilic Rectal AZA Foam

To 948.4 g of purified distilled water containing 1.4 g and 0.14 g of methyl- and propylparaben respectively as preservatives; 2.0 g KELTROL TF (xanthan gum, suspending agent) were added and dispersed. Then 2.0 g of SOYA LECITHIN emulsifying agent (unbleached) were also dispersed as well as 5.0 g of carbomer (CARBOPOL 974 P NF). The carbomer was then neutralized with 2 g of sodium hydroxide dissolved in 20 ml of purified water (pH 7.10). Then 10.0 g of POLYSORBATE 80 (surfactant) were added to the mixture along with 0.250 g CITRAL (perfume) and the two components were dispersed. Finally, 2.366 g of AZA were added and also dispersed. The theoretical content of Azathioprine in this formulation was 50 mg/21 g of mixture. Viscosity of the concentrate measured in Brookfield-viscometer DV-II at 20° C. and 12 rpm using spindle 64 was: 29, 700 CPS.

The concentrate was then mixed with n-butane (foaming agent) using standard equipment for the preparation of aerosols. The n-butane content in the aerosol mixture was 2.5%. The mixture was then filled into canisters of the Sepro bag-in-can type (containing a collapsible lamipack bag mounted on a valve and fitted into a monoblock aluminum can: the propellant was nitrogen present in the monoblock and thus separated from the aerosol concentrate of the bag). The can was equipped with a nozzle and a canula. The delivered amount of concentrate per canister was 21±1 g leading to 200–220 ml of foam at 37° C.

EXAMPLE 2

Hydrophobic Rectal AZA Foam

To 948.45 g of purified distilled water containing 1.43 g and 0.14 g of methyl- and propylparaben respectively: 2.0 g of KELTROL TF (xanthan gum, suspending agent); 2.0 g of unbleached SOYA LECITHIN (emulsifying agent); 5.0 g of CARBOPOL 974 P NF (carbomer) were added and dispersed with a SILVERSON homogenizer. The carbomer was neutralized with 2.0 g of sodium hydroxide dissolved in 20 ml of purified distilled water, pH 7.05.

Then 47.40 g WITEPSOL H 15 (Hard Fat NF) an hydrophobing agent were added and very efficiently dispersed in the mixture using a SILVERSON homogenizer. A creamy concentrate having an hydrophobic feel was obtained.

10.50 g of POLYSORBATE 80 (surfactant) and 0.25 g CITRAL (perfume) were added and also dispersed with the homogenizer. To stabilize this emulsion and particularly the corresponding foam, 20.80 g of POLAWAX NF (as non-ionic emulsifying wax) were added and dispersed in the mixture. Finally 1.93 g of AZA was added and also dispersed. The theoretical content of the Azathioprine in the formulation was 50 mg in 27.5 g of mixture. Viscosity of the concentrate measured as for AZA-1:41,000 CPS. The concentrate was then mixed with n-butane (foaming agent) as for sample AZA-1, n-butane content: 2.5%. The mixture was then filled into canisters of the Sepro bag-in-can type. The delivered amount of concentrate per canister was 27.5 g±1 g leading to 205–220 ml of foam at 37° C. The hydrophobic foam had a lower expansion ratio than the hydrophilic foam.

EXAMPLE 3

Preparation of AZA Enteric-Coated Capsules

1 IMURAN tablet (50 mg Azathioprine tablet containing 50 mg AZA (Burroughs Wellcome Co.) was crushed in a mortar; and the powder was filled in a size 2 hard gelatin capsules. The capsules were closed manually. Each capsule was weighed individually (IPC)

The capsules were banded on a laboratory type banding machine with a 50 wt % solution of gelatin in water (1% polysorbate 80). The capsule was finally coated in a laboratory coating machine by the spraying with an aqueous solution of Eudragit S-100 (1N NH$_4$OH). The finished capsules (12 wt-% Eudragit) were resistant to artificial gastric juice (pH 1.2) for 2 hours, but disintegrated in artificial gut juice (pH 7.2) in no more than 60 minutes.

EXAMPLE 4

Topical Colonic Administration of AZA

A. Subjects: Twenty-four healthy human volunteers were recruited and screening physical exam and laboratory studies (complete blood count, chemistry panel, and urinalysis) were performed. Prior to study entry, the erythrocyte thiopurine methyltransferase (TPMT) activity was determined in all patients and subjects with homozygous or heterozygous low TPMT activity were excluded from the study because of prior reports of severe neutropenia associated with AZA or 6MP use in this population. Subjects were screened for medical conditions or a surgical history which could impact AZA absorption or its metabolism. Demographics of subject group are summarized in Table 1. There were no statistically significant differences between the groups for the parameters indicated.

TABLE 1

| Group | Number | Age (yr) | Weight (kg) | TPMT level (Units/ml RBC) |
| --- | --- | --- | --- | --- |
| Oral | 6 | 27.7 ± 7.5 | 80.3 ± 20.0 | 21.9 ± 2.3 |
| DRO | 6 | 36.7 ± 18.5 | 87.9 ± 44.0 | 21.2 ± 2.6 |
| HBF | 6 | 29.2 ± 5.8 | 83.7 ± 11.6 | 23.5 ± 4.0 |
| HPF | 6 | 33.2 ± 8.2 | 71.7 ± 10.0 | 19.5 ± 1.8 |

*mean ± SD

B. Study Design: The 24 healthy human subjects were randomly assigned to receive 50 mg of one of four AZA dosage formulations (each n=6): oral: delayed-release oral (DRO); hydrophobic rectal foam (HBF); and hydrophilic rectal foam (HPF). All subjects also received a 50 mg does of intravenous (IV) AZA. The two doses of AZA were separated by at least 3 weeks and the order of dosing (IV vs. non-IV) was randomly determined. Subjects fasted after midnight the night prior to the study. If rectal foam were to be administered, subjects were given a Fleet's enema if they had not had a bowel movement the morning of the study.

The intravenous dose (see below) was administered as an infusion diluted in 20 ml of normal saline and delivered over 5 minutes. The oral preparations were administered with a sip of water. Rectal formulations were administered by a nurse. Subjects remained fasting for three hours following dose administration. A time zero blood sample was obtained prior to the study. After dose administration or after initiation of the IV infusion, blood samples were drawn in 7 ml EDTA ($K_3$)-containing vacuum tubes (Sherwood Medical, St. Louis, Mo.) at the following time intervals: 5, 10, 15, 30 minutes and 1, 1.5, 2, 3, 4, 5, 6, and 8 hours.

The AZA pharmacokinetics were studied by determining 6MP bioavailability rather than AZA bioavailability because of the availability of reliable techniques for measuring plasma 6MP levels. In addition, 6MP is the more biologically relevant molecule, as AZA functions as a prodrug for 6MP. Following absorption, AZA is quickly converted to 6MP via non-enzymatic attack on the bond between the imidazole ring and the 6MP molecule by sulfhydryl-containing compounds such as glutathione. 6MP is then metabolized to compounds with immunomodulatory activity, the 6-thioguanine nucleotides (6TGN).

C. Determination of 6MP concentration in Plasma: Immediately after collection, blood samples were placed in an ice-water slurry. Within 30 minutes the blood sample was centrifuged for 10 minutes at 1000 g, 4° C. Plasma was then transferred to plastic cryotubes (Nunc Inc., Naperville, Ill.) and stored at −70° C. until analysis. 6MP concentrations were determined by HPLC using the technique of Zimm (20) with modifications. Solid phase extraction columns (C18 Sep-Paks, Waters, Inc., Millford, Mass.) were sequentially pre-rinsed with 2.5 ml of methanol and 5 ml of 0.2% acetic acid. One ml of plasma was loaded onto the Sep-Pak following addition of 0.04 ml of saturated EDTA·2Na (Aldrich, Milwaukee, Wis.) solution to the plasma. Dithiothreitol (DTT) was not included because AZA is immediately converted to 6MP in the presence of DTT. The cartridges were rinsed with 2 ml of 0.2% acetic acid and then centrifuged at 3200 rpm for 5 minutes to remove excess water. The samples were eluted from the cartridges with 2 ml of methanol and evaporated to dryness under a stream of nitrogen at 37° C. Samples were then reconstituted in 200 uL of mobile phase, vortexed for 30 seconds, transferred to 1.5 ml conical microfuge tubes and centrifuged in a microcentrifuge for 5 minutes. A portion (0.175 ml) of supernatant was transferred to HPLC vials.

6MP levels were then determined by HPLC. The analytical column was a Hewlett-Packard (Rockville, Maryland) octadecylsilane (ODS) Hypersil, 200×4.6 mm, 5 μm particle size. It was protected by a Zorbax (Mac-mod Analytical, Chadds Ford, Pennsylvania) ODS 4×12.5 mm guard column. The mobile phase was 0.8% acetonitrile in 1 mM triethylamine, adjusted to pH 3.2 with phosphoric acid. Absorbance was monitored at 340 nm. The injection volume was 80 uL. Unknowns were determined by comparing them to a standard curve constructed the same day by adding known quantities of 6MP to blank plasma. The lower limit of quantification of 6MP was 2 ng/ml. The mean calculated concentration ±coefficient of variation for the 2 ng/ml and 50 ng/ml standards were 2.0 ng/ml ±18% and 50.2 ng/ml±3.4%, respectively.

D. Study Medications: 1) Intravenous AZA, lyophilized as the sodium salt (Burroughs Wellcome, Research Triangle Park, N.C.). 2) Standard 50 mg oral tablet (Burroughs Wellcome, Research Triangle Park, N.C.). 3) Delayed-release 50 mg oral tablet (DRO). 4) Hydrophobic rectal form (HBF). Administered rectally via a pressurized foam canister. 50 mg of AZA (Fermion/Orion Corporation, Espoo, Finland) is dissolved in a dose of foam containing witepsol H15 (an oleagenous base) to make it hydrophobic. 5) Hydrophilic rectal foam. Administered rectally via a pressurized foam canister. 50 mg of AZA (Fermion/Orion Corporation, Espoo, Finland) is dissolved in a foam. The delayed-release oral and rectal foam forms of AZA were prepared by Tillotts Pharma A.G. (Ziefen, Switzerland).

E. Results:

1. Pharmacokinetic Parameters for IV Dosing:

The AUC, CL, $V_{ds}$, and $T_{1/2}$ (mean±SD) for all 24 subjects following 50 mg AZA administered intravenously are listed in Table 2.

TABLE 2

PHARMACOKINETIC PARAMETERS FOR 6MP FOLLOWING 50 MG OF AZA ADMINISTERED INTRAVENOUSLY TO 24 HEALTHY VOLUNTEERS*

| AUC (ng.hr/ml) | CL (L/kg.hr) | $V_{ds}$ (L/kg) | $T_{1/2}$ (hr) |
| --- | --- | --- | --- |
| 100.7 ± 30.5 | 3.8 ± 1.2 | 6.7 ± 3.1 | 1.2 ± 0.37 |

*mean ± SD

2. Pharmacokinetic Parameters for Colonic Delivery:

The AUC, F, $T_{MAX}$, and $C_{MAX}$ (mean±SE) for each of the non-IV delivery routes are listed in Table 3. The mean bioavailability of the oral preparation was significantly greater than for the other preparations, and the mean $T_{MAX}$ of the DRO formulation was significantly greater than for the other formulations. None of the other differences were statistically significant.

TABLE 3

PHARMACOKINETIC PARAMETERS FOR 6MP FOLLOWING 50 MG AZA ADMINISTERED VIA ORAL, DRO, HBF AND HPF*

| Group (n = 6) | AUC (ng.hr/ml) | F (%) | $T_{MAX}$ (hr) | $C_{MAX}$ (ng/ml) |
|---|---|---|---|---|
| Oral | 55 ± 27 | 52 ± 26 | 1.8 ± 0.8 | 21 ± 13 |
| DRO | 11 ± 9 | 13 ± 15 | 5.4 ± 0.2$^c$ | 5 ± 5$^c$ |
| HBF | 5 ± 4 | 5 ± 4 | 2.1 ± 0.3$^d$ | 2 ± 1$^d$ |
| HPF | 3 ± 4 | 2 ± 3 | 2.0 ± 0.0$^e$ | 1 ± 1$^e$ |
| P value | 0.01$^a$ | 0.01$^a$ | 0.01$^b$ | 0.01$^a$ |

$^a$P values derived by analysis of covariance. Post-hoc tests (Duncan's): a-oral > DRO = HBF = HPF; b-DRO > oral = HBF = HPF. c-mean ± SE of the 5 subjects with detectable concentrations of 6MP. d-mean ± SE of the 4 subjects with detectable concentrations of 6MP. e-mean ± SE of the 3 subjects with detectable concentrations of 6MP.
*mean ± SE 3. Rectal Administration The rectal foam preparations were well-tolerated. Twenty-two of the subjects retained the foam for greater than 6 hours. One subject reported expelling the hydrophobic foam after one hour and another reported expelling the hydrophobic foam after two hours. The subject who reported expelling the foam after one hour did not have detectable absorbtion. The subject who reported expelling the foam after 2 hours had a $C_{MAX}$ of 2.35 ng/ml at 3 hours. No adverse reactions to the foam preparations were reported.

F. Discussion: This example demonstrates that the systemic bioavailability of 6MP following dosing with delayed-release oral and rectal delivery formulations of AZA is significantly lower than the bioavailability of 6MP after standard oral AZA. There are several potential factors contributing to this observation. The most likely is that the absorbtion of AZA across the colonic mucosa is reduced compared to absorbtion across gastric and small intestinal mucosa due to absence of specific transport mechanisms or differing rates of passive absorbtion. Reduced colonic absorbtion compared to jejunal absorbtion has been demonstrated for 5-aminosalicylate (5-ASA) (S. Bondesen et al., *Br. J. Clin. Pharm.*, 25, 269 (1988)). AZA and 6MP may be more completely metabolized in the colonic mucosa of the more proximal GI tract. In addition, some AZA may be lost in the stool. Fecal excretion of 5-ASA following administration of Eudragit-coated tablets is approximately 25% (B. Norlander et al., *Aliment. Pharmacol. Therap.*, 4, 497 (1990)).

Following absorbtion, AZA is quickly converted to 6MP in plasma. This conversion occurs as the result of non-enzymatic attack by sulffhydril-containing compounds such as glutathione on the bond between the 6MP molecule and the imidazole ring of AZA (L. Lennard et al., *Clin. Pharmacol. Ther.*, 46, 149 (1989)). Glutathione is present in every mammalian cell, including colonic epithelial cells and lymphocytes, and prior studies have shown that lymphocytes contain the enzymes necessary to convert 6MP to the active metabolites, the 6TGNs (B. Bostrom et al., *Am. J. Ped. Hem./Onc.*, 15, 80 (1993)). It is, therefore, reasonable to expect that topical delivery of AZA will result in local inmmunosuppressive effects on colonic lymphocytes.

This example demonstrates that colonic delivery of AZA results in significantly less 6MP bioavailability that standard oral AZA. It is believed that colonic delivery of AZA can reduce the drug's toxicity by reducing systemic exposure to 6MP. In addition, this topical form of AZA administration can allow delivery of higher, locally concentrated doses to intraepithelial and lamina propria colonic lymphocytes.

EXAMPLE 5

Treatment of Patient at Risk for Colorectal Polyps

A patient is identified as being at risk for development of colorectal adenomas or cancer due to either prior history of colorectal adenomatous polyps or the presence of other conditions associated with at-risk patients. Delayed release of oral azathioprine is administered at a dose of 150–1000 mg/day to prevent the recurrence or primary development of colorectal adenomatous polyps. The delayed release azathioprine is well-tolerated and results in minimal systemic absorption.

All publications and patents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An enema formulation comprising an amount of azathioprine effective to prevent colorectal adenomas without dose-limiting system toxicity, in combination with a flowable carrier, and having a core of azathioprine that is released in the lower intestinal tract.

2. An enema formulation comprising an amount of azathioprine effective to prevent colorectal adenomas without dose-limiting system toxicity, in combination with a flowable carrier, and having enterically-coated microparticles of azathioprine that are released in the lower intestinal tract.

3. An enterically-coated unit dosage form adapted for oral administration, comprising an amount of azathioprine effective to prevent colorectal adenomas without dose-limiting system toxicity, wherein the azathioprine is released in the terminal portion of the ileum and the colon.

* * * * *